US008632988B1

(12) United States Patent
Skaar et al.

(10) Patent No.: US 8,632,988 B1
(45) Date of Patent: Jan. 21, 2014

(54) PATHOGEN HEMOGLOBIN RECEPTOR SPECIFICITY FOR HUMAN HEMOGLOBIN

(75) Inventors: Eric P. Skaar, Brentwood, TN (US); Glib Pishchany, Antioch, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/333,798

(22) Filed: Dec. 21, 2011

Related U.S. Application Data

(60) Provisional application No. 61/425,588, filed on Dec. 21, 2010.

(51) Int. Cl.
*G01N 33/569* (2006.01)
*G01N 33/53* (2006.01)
*C12P 1/00* (2006.01)
*C07K 1/00* (2006.01)

(52) U.S. Cl.
USPC ............ 435/7.33; 435/7.2; 435/7.1; 435/267; 435/269

(58) Field of Classification Search
None
See application file for complete search history.

(56) References Cited

PUBLICATIONS

Bullen, J. J. (1981). The significance of iron in infection. Rev. Infect. Dis. 3, 1127-1138.
Cheng, A. G., Kim, H. K., Burts, M. L., Krausz, T., Schneewind, O., and Missiakas, D. M. (2009). Genetic requirements for *Staphylococcus aureus* abscess formation and persistence in host tissues. Faseb J. 23, 3393-3404.
Crosa J. H., Mey A. R., and Payne S. M. (2004). Iron Transport in Bacteria (Washington, D.C.: A.S.M. Press).
Drabkin, D. (1951). Metabolism of the Hemin Chromoproteins. Physiological Reviews 31, 345-431.
Dryla, A., Hoffmann, B., Gelbmann, D., Giefing, C., Hanner, M., Meinke, A., Anderson, A. S., Koppensteiner, W., Konrat, R., von Gabain, A., and Nagy, E. (2007). High-affinity binding of the staphylococcal HarA protein to haptoglobin and hemoglobin involves a domain with an antiparallel eight-stranded beta-barrel fold. J. Bacteriol. 189, 254-264.
Duthie, E. S., and Lorenz, L. L. (1952). Staphylococcal coagulase ; mode of action and antigenicity. J. Gen. Microbiol. 6, 95-107.
Hardison, R. C., Chui, D. H., Giardine, B., Riemer, C., Patrinos, G. P., Anagnou, N., Miller, W., and Wajcman, H. (2002). HbVar: A relational database of human hemoglobin variants and thalassemia mutations at the globin gene server. Hum. Mutat. 19, 225-233.
Johansson, L., Rytkonen, A., Bergman, P., Albiger, B., Kallstrom, H., Hokfelt, T., Agerberth, B., Cattaneo, R., and Jonsson, A. B. (2003). CD46 in meningococcal disease. Science 301, 373-375.
Klevens, R. M., Morrison, M. A., Nadle, J., Petit, S., Gershman, K., Ray, S., Harrison, L. H., Lynfield, R., Dumyati, G., Townes, J. M., et al. (2007). Invasive methicillin-resistant *Staphylococcus aureus* infections in the United States. Jama 298, 1763-1771.
Kuehnert, M. J., Hill, H. A., Kupronis, B. A., Tokars, J. I., Solomon, S. L., and Jernigan, D. B. (2005). Methicillin-resistant-*Staphylococcus aureus* hospitalizations, United States. Emerg. Infect. Dis. 11, 868-872.
Lecuit, M., Vandormael-Pournin, S., Lefort, J., Huerre, M., Gounon, P., Dupuy, C., Babinet, C., and Cossart, P. (2001). A transgenic model for listeriosis: role of internalin in crossing the intestinal barrier. Science 292, 1722-1725.
Legrand, N., Ploss, A., Balling, R., Becker, P. D., Borsotti, C., Brezillon, N., Debarry, J., de Jong, Y., Deng, H., Di Santo, J. P., et al. (2009). Humanized mice for modeling human infectious disease: challenges, progress, and outlook. Cell Host Microbe 6, 5-9.
Maresso A.W., Garufi G., and Schneewind O. (2008). *Bacillus anthracis* secretes proteins that mediate heme acquisition from hemoglobin. PLoS Pathog. 4, e1000132Mazmanian, S. K., Liu, G., Jensen, E. R., Lenoy, E., and Schneewind, O. (2000). *Staphylococcus aureus* sortase mutants defective in the display of surface proteins and in the pathogenesis of animal infections. Proc. Natl. Acad. Sci. U S A 97, 5510-5515.
Mazmanian, S. K., Skaar, E. P., Gaspar, A. H., Humayun, M., Gornicki, P., Jelenska, J., Joachmiak, A., Missiakas, D. M., and Schneewind, O. (2003). Passage of heme-iron across the envelope of *Staphylococcus aureus*. Science 299, 906-909.
Muryoi, N., Tiedemann, M. T., Pluym, M., Cheung, J., Heinrichs, D. E., and Stillman, M. J. (2008). Demonstration of the iron-regulated surface determinant (Isd) heme transfer pathway in *Staphylococcus aureus*. J. Biol. Chem. 283, 28125-28136.
Pishchany, G., Dickey, S. E., and Skaar, E. P. (2009). Subcellular localization of the *Staphylococcus aureus* heme iron transport components IsdA and IsdB. Infect. Immun. 77, 2624-2634.
Reniere, M. L., and Skaar, E. P. (2008). *Staphylococcus aureus* haem oxygenases are differentially regulated by iron and haem. Mol. Microbiol. 69, 1304-1315.
Reniere, M. L., Torres, V. J., and Skaar, E. P. (2007). Intracellular metalloporphyrin metabolism in *Staphylococcus aureus*. Biometals 20, 333-345.
Reniere, M. L., Ukpabi, G. N., Harry, S. R., Stec, D. F., Krull, R., Wright, D. W., Bachmann, B. O., Murphy, M. E., and Skaar, E. P. (2010). The IsdG-family of haem oxygenases degrades haem to a novel chromophore. Mol. Microbiol. 75, 1529-1538.
Romero, J. R., Suzuka, S. M., Nagel, R. L., and Fabry, M. E. (2004). Expression of HbC and HbS, but not HbA, results in activation of K-Cl cotransport activity in transgenic mouse red cells. Blood 103, 2384-2390.
Shultz, L. D., Ishikawa, F., and Greiner, D. L. (2007). Humanized mice in translational biomedical research. Nat. Rev. Immunol. 7, 118-130.
Skaar, E. P., Humayun, M., Bae, T., DeBord, K. L., and Schneewind, O. (2004). Iron-source preference of *Staphylococcus aureus* infections. Science 305, 1626-1628.

(Continued)

*Primary Examiner* — S. Devi
(74) *Attorney, Agent, or Firm* — Stites & Harbison PLLC; Mandy Wilson Decker

(57) ABSTRACT

A method of measuring binding between hemoglobin and a microbe of interest includes: providing hemoglobin from a source of interest; contacting the hemoglobin with a microbe of interest; and measuring the binding affinity between the hemoglobin and the microbe, wherein the binding affinity is indicative of microbe virulence in the presence of the hemoglobin.

5 Claims, 7 Drawing Sheets

(56) References Cited

PUBLICATIONS

Sun, H., Ringdahl, U., Homeister, J. W., Fay, W. P., Engleberg, N. C., Yang, A. Y., Rozek, L. S., Wang, X, Sjobring, U., and Ginsburg, D. (2004). Plasminogen is a critical host pathogenicity factor for group A streptococcal infection. Science 305, 1283-1286.

Taylor J. M., and Heinrichs D. E. (2002). Transferrin binding in *Staphylococcus aureus*: involvement of a cell wall-anchored protein. Mol. Microbiol. 43, 1603-1614.

Torres, V. J., Attia, A. S., Mason, W. J., Hood, M. I., Corbin, B. D., Beasley, F. C., Anderson, K. L., Stauff, D. L., McDonald, W. H., Zimmerman, L. J., et al. (2010). *Staphylococcus aureus* Fur regulates the expression of virulence factors that contribute to the pathogenesis of pneumonia. Infect. Immun. 78, 1618-1628.

Torres, V. J., Pishchany, G., Humayun, M., Schneewind, O., and Skaar, E. P. (2006). *Staphylococcus aureus* IsdB is a hemoglobin receptor required for heme iron utilization. J. Bacteriol. 188, 8421-8429.

Weems, J. J., Jr. (2001). The many faces of *Staphylococcus aureus* infection. Recognizing and managing its life-threatening manifestations. Postgrad. Med. 110, 24-26, 29-31, 35-26.

Ye L., Chang J.C., Lu R., and Kan Y.W. (2008). High oxygen environment during pregnancy rescues sickle cell anemia mice from prenatal death. Blood Cells Mol. Dis. 41, 67-72.

Zhu, H., Xie, G., Liu, M., Olson, J. S., Fabian, M., Dooley, D. M., and Lei, B. (2008). Pathway for heme uptake from human methemoglobin by the iron-regulated surface determinants system of *Staphylococcus aureus*. J. Biol. Chem. 283, 18450-18460.

PATHOGEN HEMOGLOBIN RECEPTOR SPECIFICITY FOR HUMAN HEMOGLOBIN

RELATED APPLICATIONS

This application claims priority from U.S. Provisional Application Ser. No. 61/425,588 filed Dec. 21, 2010, the entire disclosure of which is incorporated herein by this reference.

GOVERNMENT SUPPORT CLAUSE

This invention was made with government support under grant numbers AI069233 and AI073843 awarded by the National Institute of Allergy and Infection Diseases. The government has certain rights in the invention.

TECHNICAL FIELD

The presently-disclosed subject matter relates to the study, screening, and treatment of microbial infections. In particular, the presently-disclosed subject matter relates to the study, screening, and treatment of microbial infections in humans.

INTRODUCTION

Vertebrates sequester nutrients required for microbial multiplication as a defense against infection in a process termed nutritional immunity (Bullen, 1981). In turn, pathogens have evolved intricate mechanisms to overcome this host defense and acquire needed nutrients. Iron is one such nutrient that is vital to the host-pathogen interaction (Crosa et al., 2004). In vertebrates, the majority of iron is bound by intracellular iron-binding proteins. Iron that is released upon cell lysis is bound by circulating transferrin ensuring that the level of available iron in the serum is incompatible with bacterial replication. In order to grow within vertebrates, bacterial pathogens must liberate intracellular iron and compete with host iron-sequestering proteins.

*S. aureus* has multiple iron acquisition systems including proteins involved in the acquisition of both siderophore-iron and heme-iron. The most abundant source of iron within vertebrates is hemoglobin (Drabkin, 1951). To access this iron source, *S. aureus* lyses erythrocytes through the secretion of hemolytic toxins (Torres et al., 2010). Upon erythrocyte lysis, *S. aureus* binds hemoglobin on the surface of the bacterial cell wall. The iron-containing heme co-factor is then extracted from hemoglobin and passed through the cell envelope into the cytoplasm where heme is degraded to release iron. This entire process is carried out by members of the Iron-regulated Surface Determinant system (Isd), which are up-regulated during conditions of iron starvation (Mazmanian et al., 2003; Muryoi et al., 2008; Pishchany et al., 2009; Reniere and Skaar, 2008; Reniere et al., 2007; Reniere et al., 2010; Skaar et al., 2004; Torres et al., 2006; Zhu et al., 2008). The importance of the Isd system to iron acquisition and staphylococcal pathogenicity has been demonstrated using murine models of infection (Cheng et al., 2009; Mazmanian et al., 2000; Pishchany et al., 2009; Torres et al., 2006).

A critical step in heme-iron acquisition is the capture of hemoglobin by the hemoglobin receptor IsdB (Mazmanian et al., 2003; Pishchany et al., 2009; Torres et al., 2006). This process is required for pathogenesis as demonstrated by the decreased proliferation of *S. aureus* strains inactivated for isdB in murine models. Notably, the primary amino acid sequence of hemoglobin differs across species and variation within hemoglobin primarily localizes to surface exposed residues that are likely recognized by IsdB (FIG. 5A). Therefore, interspecies variation within hemoglobin may affect its capture by *S. aureus* and subsequently impact host range.

SUMMARY

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter is based, in part, on the discovery that the hemoglobin receptors of certain microbes preferentially recognize human hemoglobin (and the hemoblobin of higher vertebrates) (hHb) as compared to hemoglobins from other animal species, such as mice. For example, *Staphylococcus aureus* (*S. aureus*) IsdB preferentially binds hemoglobin derived from humans, and does so with a stronger affinity than mouse hemoglobin. As disclosed herein, increased binding of hHb facilitates iron acquisition by *S. aureus* and increased iron availability exacerbates *S. aureus* infection. In this regard, the presently-disclosed subject matter includes a method of studying infection using an animal model expressing hHb, for example a hHb-expressing mouse.

The preferential recognition of hHb by the hemoglobin receptors of certain microbes results in enhanced microbe proliferation and increased susceptibility to infection. As disclosed herein, the present inventors further contemplate that distinctions in the hHb sequence of particular subjects results in variable susceptibility to certain microbes. Without wishing to be bound by theory or mechanism, it is contemplated that susceptibility to a particular microbe correlates to the binding affinity of the hemoglobin receptor of the microbe to the particular hHb sequence of the subject. In this regard, the presently-disclosed subject matter includes a screening method for determining susceptibility of a subject to infection. The presently-disclosed subject matter further includes a method of treating subjects who are susceptible to infection, for example, treatment of susceptible subjects prior to the occurrence of an increased risk of exposure to the microbe.

The presently-disclosed subject matter includes a method of measuring binding between hemoglobin and a microbe of interest, including: providing hemoglobin from a source of interest; contacting the hemoglobin with the microbe; and measuring the binding affinity between the hemoglobin and the microbe, wherein the binding affinity is indicative of microbe virulence in the presence of the hemoglobin.

In some embodiments of the methods described herein, the microbe is a bacteria, a fungi, or a parasite. In some embodiments, the microbe is a pathogen that preferentially infects humans. IN some embodiments, the microbe is a pathogen selected from the group consisting of: *Mycobacterium leprae* (leprosy), *Neisseria gonorrhoeae* (gonorrhea), *Neisseria meningitidis* (meningitis), *Corynebacterium diphtheriae* (diphtheria), *Treponema* palidum (syphilis), *Salmonella typhi* (typhoid fever), and *Chlamydia trachomatis* (Chlamydia). In some embodiments, the microbe is a pathogen selected from the group consisting of: *Staphylococcus aureus, Staphylococcus lugdunensis, Staphylococcus simulans*, and *Corynebac-*

*terium diphtheriae*. In some embodiments, the pathogen is *Staphylococcus aureus*. In some embodiments, the pathogen is selected from the group consisting of: *Shigella* and *Streptococci.*

In some embodiments, the methods described herein further include comparing the binding affinity between the hemoglobin and the microbe to a control. Examples of such controls include, but are not limited to the following: an average of binding affinities between the microbe and hemoglobin from a predetermined population, a binding affinity between the microbe and human hemoglobin (hHb) having modifications identified as being associated with an increased susceptibility to the microbe; a binding affinity between the microbe and hHb lacking modifications identified as being associated with an increased susceptibility to the microbe.

In some embodiments, the binding affinity is indicative of iron acquisition by the microbe. In some embodiments, the source of interest is a subject, and binding affinity is indicative of risk of the subject developing an infection.

In some embodiments, the source of interest is hemoglobin expressed in an animal model. In some embodiments, the expressed hemoglobin is human. In some embodiments, the animal model is a mouse. In some embodiments, the source of interest is human hemoglobin expressed in a mouse model.

The presently-disclosed subject matter includes a method of screening a subject for a susceptibility to a microbe of interest, including: providing hemoglobin from a subject; contacting the hemoglobin with the microbe; and measuring the binding affinity between the hemoglobin and the microbe, wherein the binding affinity is indicative of the susceptibility of the subject to the microbe.

In some embodiments of the methods described herein, the microbe is a bacteria, a fungi, or a parasite. In some embodiments, the microbe is a pathogen that preferentially infects humans. IN some embodiments, the microbe is a pathogen selected from the group consisting of: *Mycobacterium leprae* (leprosy), *Neisseria gonorrhoeae* (gonorrhea), *Neisseria meningitidis* (meningitis), *Corynebacterium diphtheriae* (diphtheria), *Treponema palidum* (syphilis), *Salmonella typhi* (typhoid fever), and *Chlamydia trachomatis* (Chlamydia). In some embodiments, the microbe is a pathogen selected from the group consisting of: *Staphylococcus aureus, Staphylococcus lugdunensis, Staphylococcus simulans*, and *Corynebacterium diphtheriae*. In some embodiments, the pathogen is *Staphylococcus aureus*. In some embodiments, the pathogen is selected from the group consisting of: *Shigella* and *Streptococci.*

In some embodiments the method further includes comparing the binding affinity between the hemoglobin and the microbe to a control. In some embodiments, the control is selected from: an average of binding affinities between the microbe and hemoglobin from a predetermined population; a binding affinity between the microbe and human hemoglobin (hHb) having modifications identified as being associated with an increased susceptibility to the microbe; and a binding affinity between the microbe and hHb lacking modifications identified as being associated with an increased susceptibility to the microbe.

In some embodiments, the subject is at an increased risk for infection, for example, due to a surgical procedure, travel, military deployment, etc.

In some embodiments, binding affinity is indicative of iron acquisition by the microbe. In some embodiments, binding affinity is indicative of risk of developing an infection. In some embodiments, binding affinity is indicative of risk of developing an exacerbated infection.

In some embodiments, the method also includes administering treatment for the microbe to the subject. In some embodiments, such treatment is prophylactic.

BRIEF DESCRIPTION OF THE DRAWINGS

(FIGS. 1A-D) Iron-starved *S. aureus* strain Newman were incubated with hemoglobin at the indicated concentrations and washed. Captured hemoglobin was eluted, subjected to SDS-PAGE, and silver stained. Representative images are shown in FIG. 5B. Bound hemoglobin was quantified based on the relative intensity of Hb bands. Relative quantities of cell-wall bound hemoglobin are expressed as percent of hHb bound by (A) wild type, (B) ΔisdB, and (C) ΔisdB+pisdB. (D) ΔisdB harboring the indicated plasmids were incubated with hemoglobin at 10 μg/ml. Insert below panel is an image of an anti-IsdB immunoblot, demonstrating cell wall IsdB expression. Means and statistical significance were calculated based on logarithmically transformed fractions. Error bars represent confidence intervals ($\alpha$=0.05); asterisks denote quantities of bound mHb statistically different from hHb supplemented at the same conditions (Student's two-tailed t-test, $P<0.05$). In panel (D) # denotes quantities that are significantly different from hHb and mHb bound by ΔisdB+pisdB (wt). Each graph is a result of three independent experiments.

(FIGS. 2 A and B) Growth of *S. aureus* Newman wild type (A) and ΔisdB (B) in liquid medium supplemented with 5 μg/ml hemoglobin as a sole source of iron was measured based on optical density at 600 nm ($OD_{600}$) over 72 hours. The graphs represent a mean of three independent experiments. Error bars represent standard deviation; asterisks denote $OD_{600}$ values upon hHb supplementation significantly different from values upon mHb supplementation at the same time point (Student's two-tailed t-test, $P<0.05$). (C) Petri dishes containing iron-restrictive agar were streaked with bacterial cultures. Disks impregnated with 10 μg of hemoglobin were placed on top of the agar and *S. aureus* growth surrounding the disks was monitored over 72 hours. Opaque gray zones around disks indicate zone of growth. The images are a representative of five independent experiments.

DESCRIPTION OF EXEMPLARY EMBODIMENTS

Figure 1:
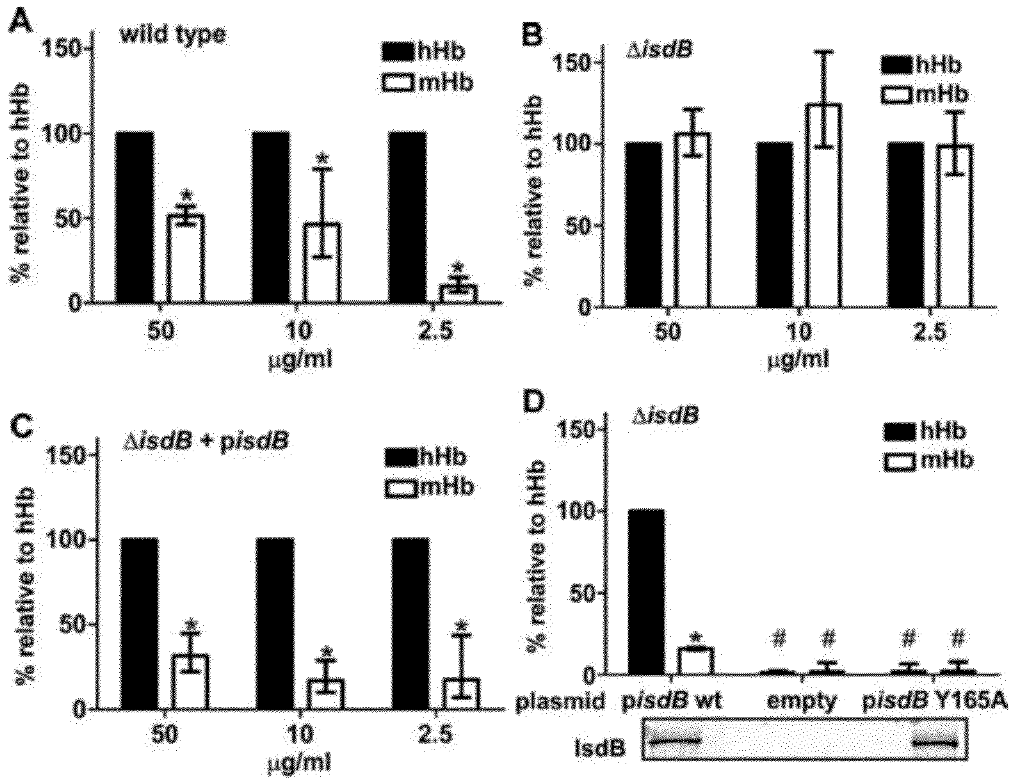
FIG. 1. *S. aureus* displays increased binding of hHb as compared to mHb.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As described herein, the present inventors surprisingly discovered that certain microbes preferentially bind hemoglobin derived from humans (hHb), as compared to hemoglobin derived from other animals. This discovery is interesting when considering prior observations, that were previously without explanation, that certain microbes preferentially infect humans. As will be known to those in the art, amino acid sequences for hHb can be obtained from databases accessible to the public, for example, the UniProt database or the GENBANK database. Such databases often have accession numbers, for example, the accession number for alpha Hb is P69905. Hb sequences included in the UniProt and GENBANK databases are expressly incorporated by reference as are equivalent and related sequences present in these or other public databases. Also expressly incorporated herein by reference are all annotations present in the databases associated with Hb. Unless otherwise indicated or apparent, the references to the databases are references to the most recent version of the databases as of the filing date of this application.

It is noted that the amino acid sequence of human hemoglobin (hHb) differs from that of hemoglobin from other sources. Indeed, individual humans can also have variations in hemoglobin amino acid sequences, which are contemplated herein to result in certain human subjects having hemoglobin to which certain microbes preferentially bind as compared to hemoglobin from different human subjects. As will be recognized by the skilled artisan, preferential binding can be shown, for example, by comparing binding affinity between a first hemoglobin polypeptide and a microbe to binding affinity between a second hemoglobin polypeptide and the microbe. As between the two, the microbe can be said to preferentially bind the hemoglobin polypeptide associated with the hemoglobin-bound-microbe having the greater binding affinity (smaller $K_D$). The present inventors further discovered that increased binding of hemoglobin by a microbe facilitates iron acquisition by the microbe, which is necessary for the microbe to thrive. The present inventors further discovered that increased availability of iron exacerbates microbe infection in a subject.

The presently-disclosed subject matter includes a method of measuring binding between hemoglobin and a microbe of interest, including: providing hemoglobin from a source of interest; contacting the hemoglobin with a microbe of interest, which can result in the formation of a hemoglobin-bound microbe; and measuring the binding affinity between the hemoglobin and the microbe, wherein the binding affinity is indicative of microbe virulence in the presence of the hemoglobin.

Microbe virulence can be assessed by considering, for example, iron acquisition by the microbe from hemoglobin from the source of interest, severity of the microbial infection, progression of the microbial infection, symptoms of the microbial infection, amount or levels of microbes, and other parameters that would be recognized by one skilled in the art upon consideration of this specification. In some embodiments, microbe virulence, and parameters for assessing same, can be considered with reference to a control.

The presently-disclosed subject matter further includes a method of screening a subject for a susceptibility to a microbe of interest, including: providing hemoglobin from a subject; contacting the hemoglobin with a microbe of interest, which can result in the formation of a hemoglobin-bound microbe; and measuring the binding affinity between the hemoglobin and the microbe, wherein the binding affinity is indicative of the susceptibility of the subject to the microbe of interest.

In some embodiments, the microbe of interest is a bacterium, a fungus, or a parasite. In some embodiments, the microbe is a pathogen that preferentially infects humans. In some embodiments, the pathogen is Shingella or Streptococci. Examples of pathogens relevant to the presently-disclosed subject matter include, but are not limited to: *Mycobacterium leprae* (leprosy), *Neisseria gonorrhoeae* (gonorrhea), *Neisseria meningitidis* (meningitis), *Corynebacterium diphtheriae* (diphtheria), *Treponema palidum* (syphilis), *Salmonella typhi* (typhoid fever), *Chlamydia trachomatis* (Chlamydia), *Staphylococcus aureus, Staphylococcus lugdunensis, Staphylococcus simulans*, and *Corynebacterium diphtheriae.*

The method of measuring binding between hemoglobin and a microbe of interest can be employed in connection with a variety of infection studies, including, but not limited to *S. aureus* pneumonia, bone infections, and endocarditis. The methods can also be used to study infectious agents that, for example, preferentially recognize human hemoglobin.

In some embodiments of the method a control is employed. For example, the method can include comparing the binding affinity between the hemoglobin and the microbe to a control. In some embodiments, the control can be human hemoglobin (hHb) having modifications or different levels of modifications (e.g., glycosylation, prenylation, other posttranslational modifications) identified as being associated with an increased susceptibility to the microbe. As noted herein, increased (or decreased) susceptibility can be assessed by measuring binding affinity between a particular hemoglobin and microbe, and can be considered relative to a control.

In some embodiments, the control can be a standard curve including binding affinities at different concentrations. In some embodiments, the control can be an average of binding affinities between the microbe and hemoglobin taken from a population of interest.

In some embodiments, the control can be modified hHb identified as being associated with an increased susceptibility to the microbe. In this regard, the present inventors contemplate that individual human subjects have hHb sequences (amino acid and nucleotide) that differ, and that such differences can be correlated to susceptibility to a microbe of interest. The present inventors further contemplate that other distinctions in hHb, such as protein modifications, can be associated with an increased susceptibility to the microbe. The presently-disclosed subject matter includes methods of identifying a risk of a subject acquiring an infection (e.g., a staphococcal infection).

In some embodiments, the source of interest of the hemoglobin is the blood of a subject. In some embodiments, the subject is human. In this regard, the presently-disclosed subject matter includes a screening method for determining susceptibility of a subject to infection.

In some embodiments, the susceptibility of the subject to the microbe is identified based on the binding affinity between the hemoglobin and the microbe. For example, in some embodiments, the microbe is *S. aureus* and susceptibility is identified wherein the $K_D$ less than about $1\times10^{-6}$ M, $5\times10^{-7}$ M, $1\times10^{-7}$ M, $5\times10^{-8}$ M, or $1\times10^{-8}$ M. In some embodiments, the microbe is *S. aureus* and susceptibility is identified wherein the $K_D$ less than about $9.8\times10^{-7}$ M $9.8\times10^{-7}$ M or wherein the $K_D$ is about $5.5\times10^{-8}$ M.

In some embodiments, the susceptibility of the subject to the microbe is identified based on the binding affinity between the hemoglobin and the microbe, as compared to a control, such as a control as described hereinabove.

In some embodiments, the human subject is at an increased risk for infection and/or exposure to a microbe. Examples of events giving rise to an increased risk include, but are not limited to, a hospital stay, a surgical procedure, participation on a sports team, or planned travel, including military deployment. It would be appropriate for such subjects to be screened to determine susceptibility of the subject to microbe(s) of interest using embodiments of the presently-disclosed subject matter.

It will be appreciated by those skilled in the art upon study of the information disclosed herein that the screening methods of the presently-disclosed subject matter can make use of various high throughput and other technologies to identify therapeutics (e.g., protein-based, small molecule based, etc.) of interest in the treatment for microbes of interest. Such therapeutics include vaccines, prophylactic therapeutics, antimicrobials, antibiotics, etc.

It will be further appreciated that the presently-disclosed subject matter provides for methods of identifying markers or biomarkers useful for determining susceptibility of a particular subject to a particular microbe. Such markers can be, for example, single nucleotide polymorphisms, single amino acid polymorphisms, nucleotide sequences or fragments, amino acid sequences of fragments, protein modifications (e.g., glycosylations), etc, e.g., distinctions in human hemoglobin sequence that are indicative of susceptibility. Hemoglobin samples collected, e.g., clinically, from various subjects are useful in this regard. Hemoglobin samples from populations thought to be at greater susceptibility to certain infections are also useful in this regard (e.g., diabetic susceptibility to *staphylococcus*). Those skilled in the art will recognize that various technologies can be used in conjunction with the subject matter disclosed herein to identify markers for susceptibility, for example, mass spectrometry, proteomic techniques, molecular biological techniques, high throughput screening techniques, etc.

In some embodiments, where the subject is identified as having an increased susceptibility to the microbe; the method also includes administration of treatment. In this regard, the presently-disclosed subject matter further includes a method of treating subjects who are susceptible to infection, for example, treatment of susceptible subjects prior to the occurrence of an increased risk of exposure to the microbe. In some embodiments, the treatment is a prophylactic treatment. In some embodiments, the treatment includes administration of an antimicrobial, e.g., antibiotic. In some embodiments, the treatment includes administration of a vaccine. In some embodiments, the treatment includes administration of an antibody to a hemoglobin receptor of the microbe. In some embodiments, the treatment includes administration of an antibody to the receptor-binding site of the hemoglobin. In some embodiments, the treatment includes administration of a therapeutic capable of disrupting the binding between the hemoblobin and the Hb binding-receptor of the microbe. In some embodiments, the therapeutic is a peptide. In some embodiments, the therapeutic is a small molecule. In some embodiments, the treatment is administered prior to the occurrence of an event placing the subject at an increased risk for contracting an infection, e.g., surgical procedure, certain travel, etc.

In some embodiments, the source of the hemoglobin is hemoglobin in an animal model. In some embodiments, the animal model expresses human hemoglobin. In this regard, the presently-disclosed subject matter includes a method of studying infection using an animal model expressing hHb, for example a hHb-expressing mouse.

The presently-disclosed subject matter is further illustrated by the following specific but non-limiting examples. The following examples may include compilations of data that are representative of data gathered at various times during the course of development and experimentation related to the present invention.

EXAMPLES

Summary

Iron is required for bacterial proliferation and *Staphylococcus aureus* steals this metal from host hemoglobin during invasive infections. This process involves hemoglobin binding to the cell wall of *S. aureus*, heme extraction, passage through the cell envelope, and degradation to release free iron. Herein, an enhanced ability of *S. aureus* to bind hemoglobin derived from humans as compared to other mammals is demonstrated. Increased specificity for human hemoglobin (hHb) translates into an improved ability to acquire iron and is entirely dependent on the staphylococcal hemoglobin receptor IsdB. This feature affects the host-pathogen interaction as demonstrated by the increased susceptibility of hHb expressing mice to systemic staphylococcal infection. Interestingly, enhanced utilization of human hemoglobin is not a uniform property of all bacterial pathogens. These results demonstrate the evolution of *S. aureus* to colonize the human host and establish hHb expressing mice as an improved model for studies into *S. aureus* pathogenesis.

Results

*S. aureus* preferentially recognizes human hemoglobin.

Figure 5:
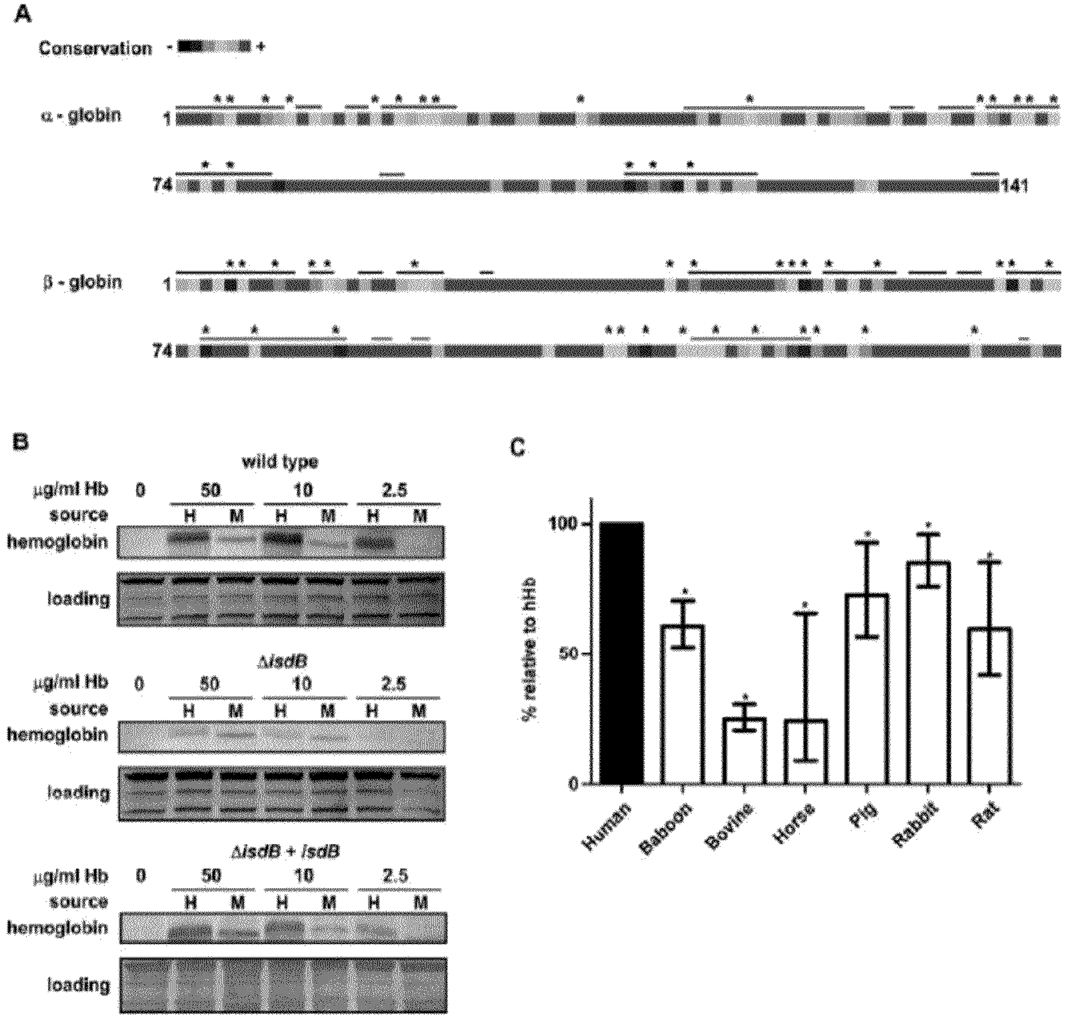
FIG. 5. Binding of hemoglobin derived from different species by *S. aureus* and amino acid conservation of hemoglobins across these species. (A) Hemoglobin amino acid conservation based on alignment of human, mouse, baboon, bovine, horse, pig, rabbit and rat sequences prepared with Lasergene 6 software. Blue indicates little conservation, while red represents absolute conservation. Surface-exposed residues are marked with black horizontal bars. Residues that are divergent between mouse and human hemoglobin are marked with asterisks. (B) Representative silver stained gels of solubilized human (H) and mouse (M) hemoglobin eluted from the cell wall of *S. aureus*. "Loading" refers to non-hemoglobin banding patterns which were used as a loading control to confirm equal loading. (C) Binding of animal hemoglobin (supplemented at 50 μg/ml) to the cell wall of *S. aureus* expressed in percent of bound human hemoglobin. Means and statistical significance were calculated based on logarithmically transformed fractions. Error bars represent confidence intervals (a=0.05); asterisks denote quantities of bound Hb statistically different from bound hHb (Student's two-tailed t-test, $P<0.05$). The graphs resulted from at least three independent experiments.

Many bacterial pathogens acquire nutrient iron from hemoglobin during infection. Interspecies variation in the primary amino acid sequence of hemoglobin suggests that bacterial pathogens may differentially recognize hemoglobin from distinct animals. Due to the extensive use of mice as animal models of *S. aureus* infections, the present inventors sought to compare the efficiencies with which *S. aureus* recognizes human (hHb) and mouse (mHb) hemoglobin. Hemoglobin was purified from fresh human or mouse blood and incubated with iron-starved *S. aureus* expressing the Isd system. Bound hemoglobin was then eluted and the relative amounts of hHb and mHb associated with the surface of *S. aureus* were compared. These experiments revealed that *S. aureus* binds hHb more effectively than mHb across a range of concentrations (FIGS. 1A and 5B).

To test whether this preferential binding is dependent on IsdB the present inventors measured relative quantities of hHb and mHb bound by an isogenic isdB mutant (ΔisdB). *S. aureus* ΔisdB fails to bind increased quantities of hHb compared to mHb and this phenotype is fully complemented by providing a full length copy of isdB in trans (FIGS. 1B, C and 5B). Cell wall expression of a mutant version of isdB containing an alanine substitution in place of the absolutely conserved tyrosine residue at position 165 eliminates hemoglobin binding, establishing this residue as being critical for hemoglobin recognition by IsdB (FIG. 1D). These results demonstrate that *S. aureus* has evolved to bind hHb through IsdB with increased efficiency compared to mHb. The hHb preference of *S. aureus* is evident amongst hemoglobins from a variety of animal species suggesting that *S. aureus* has evolved to most efficiently recognize hemoglobin from its human host (FIG. 5C).

Figure 6:
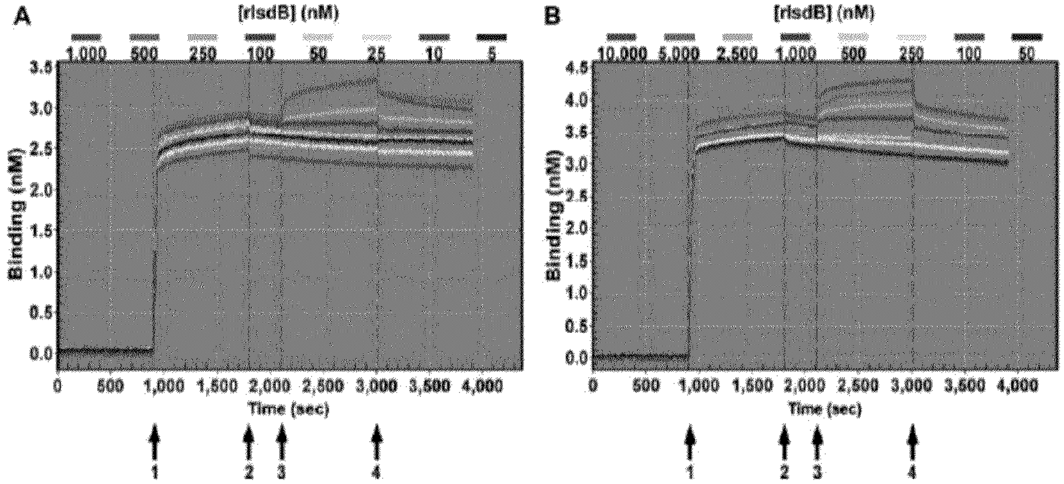
FIG. 6. Real-time in vitro binding of recombinant IsdB to hHb and mHb. Graphs depicting real-time, label-free protein association or dissociation as detected by biolayer interferometry signal of (A) rIsdB-hHb and (B) rIsdB-mHb interactions. Numbers below the graphs represent critical steps in the experiments: 1. Streptavidin sensors are placed into wells containing biotinylated hemoglobin for 900 seconds. Increase in signal indicates loading of hemoglobin. 2. Sensors are transferred into buffer to wash off unbound hemoglobin and establish a baseline (300 seconds). 3. Sensors are transferred to wells containing indicated concentrations of rIsdB (900 seconds). Increase in signal indicates association of rIsdB with hemoglobin. 4. Sensors are transferred into buffer, decrease in signal indicates dissociation of rIsdB from hemoglobin (900 seconds).

The IsdB-dependent requirement for the preferential binding of hHb to the surface of *S. aureus* suggests that IsdB binds hHb with an increased affinity as compared to mHb. To test this hypothesis, the present inventors measured the affinity of recombinant IsdB (rIsdB) for hHb and mHb by biolayer interferometry (FIG. 6). In support of the in vivo findings, the KD of the rIsdB-hHb interaction (5.5×10-8 M) is significantly stronger than the KD of the rIsdB-mHb interaction (9.8×10-7 M). Notably, this calculated affinity for the interaction of IsdB and hHb is consistent with previously published findings (Dryla et al., 2007). This result indicates that the preferential binding of hHb to the cell wall of *S. aureus* is achieved through a stronger interaction with the Hb receptor IsdB.

*S. aureus* has evolved to acquire nutrient iron from hHb more efficiently than from mHb.

Figure 2:
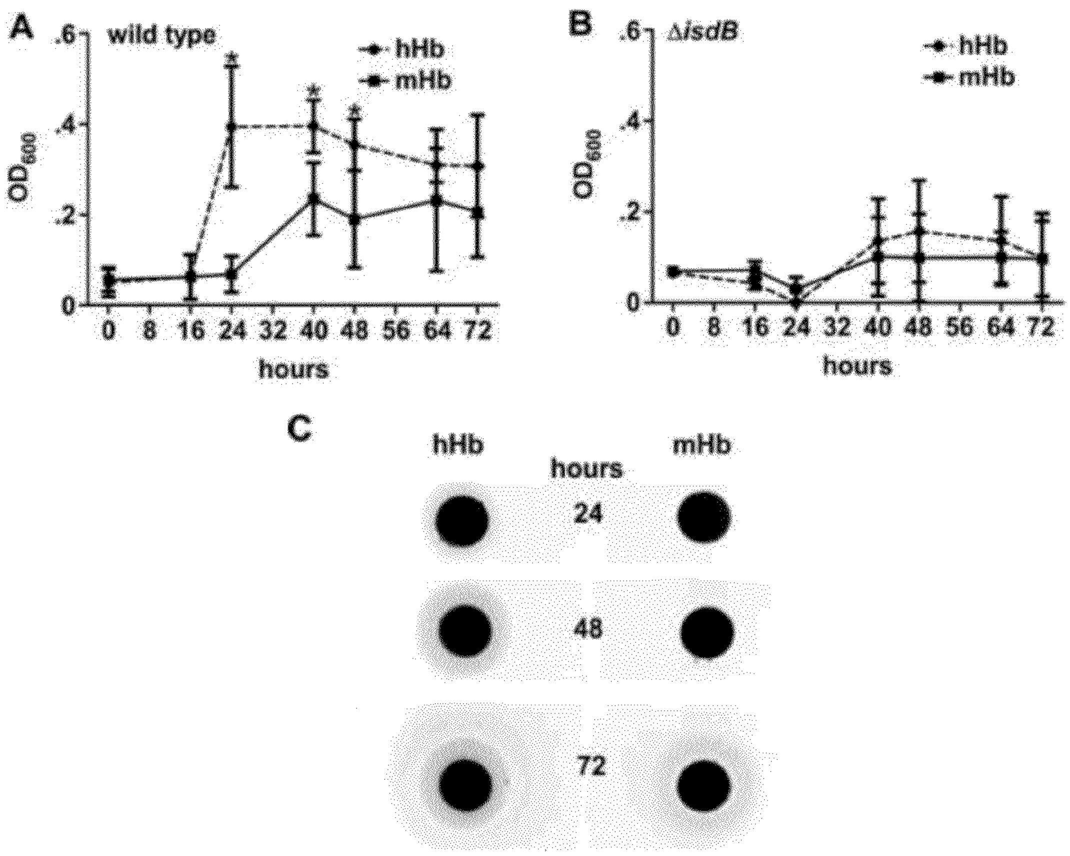
FIG. 2. hHb promotes *S. aureus* replication in iron-limiting conditions.
Figure 7:
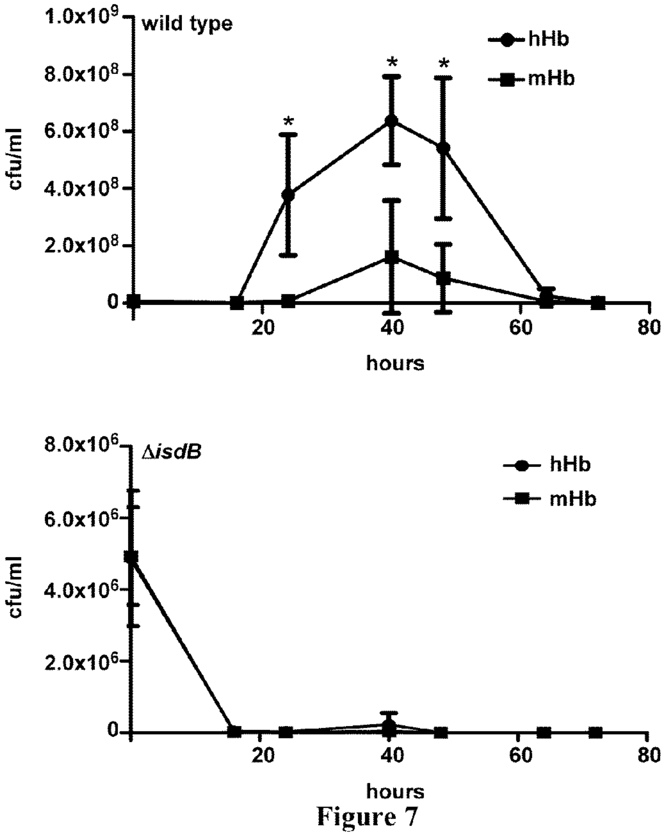
FIG. 7. Quantification of colony forming units per milliliter of medium supplemented with either hHb or mHb as an iron source over time. Colony forming units of *S. aureus* Newman and ΔisdB per milliliter of liquid medium were quantified by serial dilution followed by plating on tryptic soy agar at indicated time points over 72 hours. Liquid growth medium was supplemented with Hb at 5 μg/ml final concentration. The graphs represent a mean of three independent experiments. Error bars represent standard deviation; asterisks denote CFU/ml values upon hHb supplementation significantly different from values upon mHb supplementation at the same time point (Student's two-tailed t-test, $P<0.05$).

In iron-limiting conditions such as those encountered during infection (Pishchany et al., 2009; Reniere and Skaar, 2008), hemoglobin is a preferred source of iron that is sufficient to provide *S. aureus* with iron necessary for growth (Skaar et al., 2004; Torres et al., 2006). Therefore, the present inventors sought to determine whether preferential binding of hHb correlates with an improved ability to utilize hHb as an iron source. To test this hypothesis the present inventors measured the capacity of hHb and mHb to support *S. aureus* proliferation in an otherwise iron-deficient medium. Iron-starved *S. aureus* were inoculated into medium containing either hHb or mHb as a sole source of iron and bacterial replication was monitored over time as a function of either optical density or enumeration of colony forming units. *S. aureus* supplemented with mHb displayed a significant delay in growth as compared to hHb supplementation (FIGS. 2A and 7). These results reveal that *S. aureus* more efficiently utilizes hHb as an iron source as compared to mHb. The enhanced growth of *S. aureus* in the presence of hHb is dependent on IsdB, as indicated by ΔisdB exhibiting similar growth rates on either hHb or mHb (FIGS. 2B and 7). Notably, ΔisdB does not display an altered growth pattern when non-hemoglobin sources of iron are available (Torres et al., 2006).

To further evaluate the efficiency of hHb-iron utilization, the present inventors monitored the ability of *S. aureus* to grow on solid medium where either hHb or mHb was the sole iron source. *S. aureus* was spread on iron-deficient medium containing discs impregnated with either mHb or hHb. The zone of growth around the disks was recorded as a measure of the ability of *S. aureus* to utilize Hb as an iron source. Growth around disks containing hHb was observed by 24 hours and continued to expand over the course of the experiment. In contrast, growth was not detectable around the mHb containing disc until approximately 72 hours after inoculation (FIG. 2C). These findings demonstrate that *S. aureus* has evolved to acquire nutrient iron from hHb more efficiently than from mHb, and the enhanced recognition of hHb is mediated by the hemoglobin receptor IsdB.

Human hemoglobin exacerbates *S. aureus* infection in a murine model.

Figure 3:
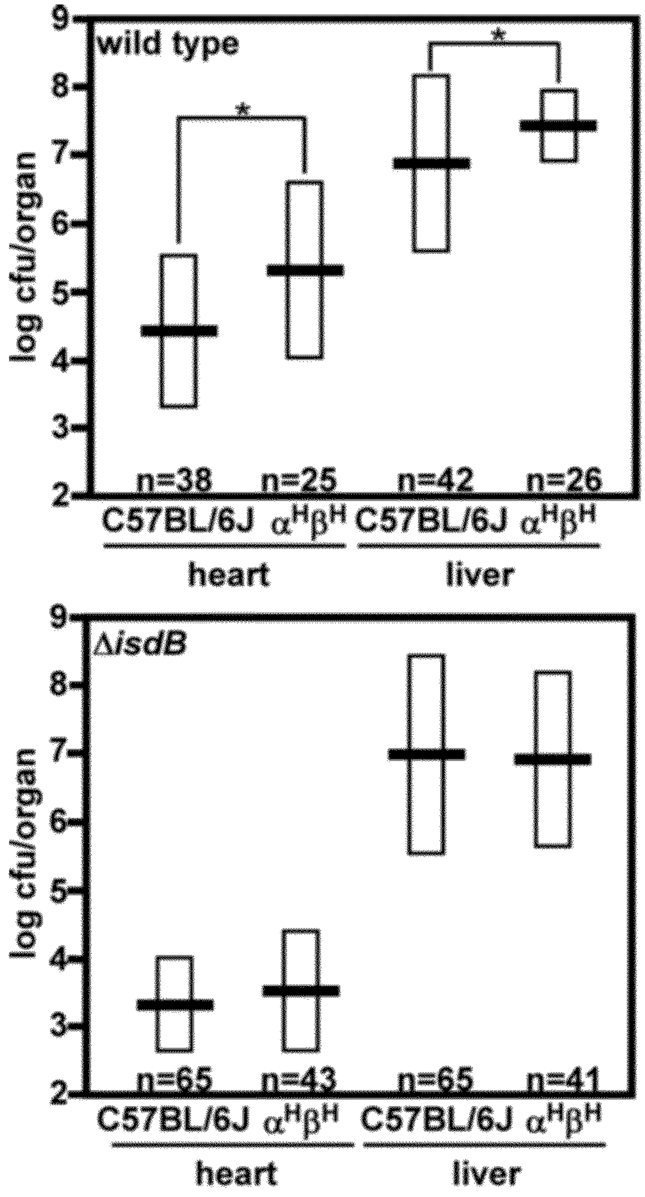
FIG. 3. Mice expressing human hemoglobin exhibit increased susceptibility to *S. aureus*. Number of colony forming units (CFU) of *S. aureus* Newman isolated from organs of systemically infected C57BL/6J and $\alpha^H\beta^A$ mice 96 hours post-inoculation as determined by serial dilution. Data were logarithmically transformed prior to statistical analyses. Horizontal bars represent the average values of CFU/organ, boxes represent standard deviation. Asterisks denote significantly different values (Student's two-tailed t-test, $P<0.05$). The graphs represent combined data acquired from multiple independent experiments.

Hemoglobin binding is a prerequisite for heme-iron acquisition during infection and as such, plays a critical role during *S. aureus* infection (Pishchany et al., 2009; Torres et al., 2006). In order to test whether the increased specificity for hHb benefits *S. aureus* during infection, the present inventors examined the susceptibility of transgenic $\alpha^H\beta^A$ mice that express normal adult human hemoglobin to systemic staphylococcal infection (Romero et al., 2004). *S. aureus* were inoculated intravenously into wild type or $\alpha^H\beta^A$ mice and the infection was allowed to proceed for 96 hours. Following this time course, mice were sacrificed, organ tissues were removed and homogenized, and bacterial counts were enumerated. In accordance with an increased ability of *S. aureus* to utilize hHb as an iron source, $\alpha^H\beta^A$ mice were more efficiently colonized as compared to wildtype animals (FIG. 3, top). The presence of human hemoglobin does not affect infection by ΔisdB as demonstrated by the similar susceptibility of wildtype and $\alpha^H\beta^A$ mice to ΔisdB (FIG. 3, bottom). Thus, the increased susceptibility of $\alpha^H\beta^A$ mice to systemic *S. aureus* infection is fully dependent on hemoglobin binding by IsdB. These results demonstrate that the enhanced specificity of *S. aureus* for hHb translates into increased colonization and establishes $\alpha^H\beta^A$ as a humanized mouse that exhibits increased susceptibility to *S. aureus* infections. Importantly, $\alpha^H\beta^A$ mice express approximately equal levels of both hHb and mHb suggesting that the effects observed here may underestimate the contribution of hHb to staphylococcal infection in humans. In addition, total Hb concentration does not differ between $\alpha^H\beta^A$ and wild type animals therefore variations in susceptibility are not due to hemoglobin abundance (data not shown). Knock-in mice that express exclusively hHb have been previously generated. However, hHb knock-in mice are notoriously difficult to breed and are therefore unsuitable for infection models, which require high numbers of subjects in order to evaluate statistical significance (Ye et al., 2008).

Preference for human hemoglobin varies across pathogens.

Figure 4:
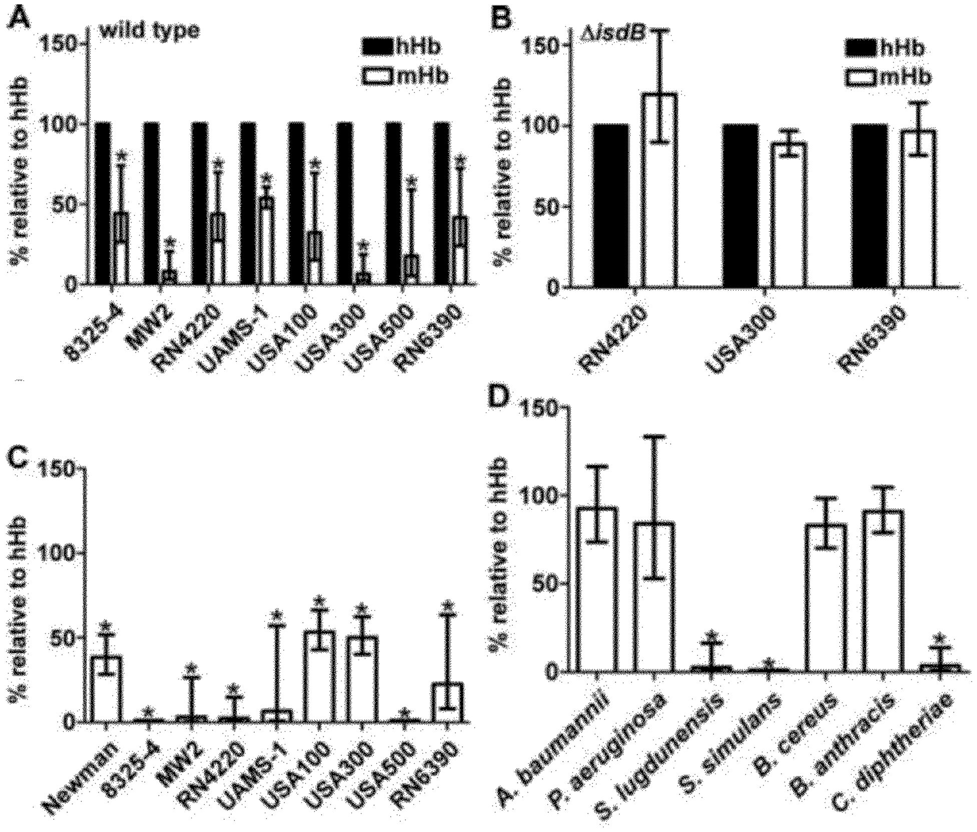
FIG. 4. Bacterial pathogens vary in preference of hHb over mHb. (A and B) Binding of hHb and mHb by *S. aureus* strains was assessed as in FIG. 1. (C and D) Petri dishes containing iron-restrictive agar were streaked with (C) strains of *S. aureus*, and (D) other bacterial pathogens. Disks impregnated with 10 μg of hHb or mHb were placed on top of the agar and bacterial growth surrounding the disks was measured. The graphs depict growth on mHb as a percentage of growth on hHb in the same conditions (growth on hHb=100%). The graphs represent a mean of three to four independent experiments. Means and statistical significance were calculated based on logarithmically transformed fractions. Error bars represent confidence intervals ($\alpha$=0.05); asterisks denote growth on mHb that is statistically different from growth on hHb supplemented at the same conditions (Student's two-tailed t-test, $P<0.05$).
Figure 8:
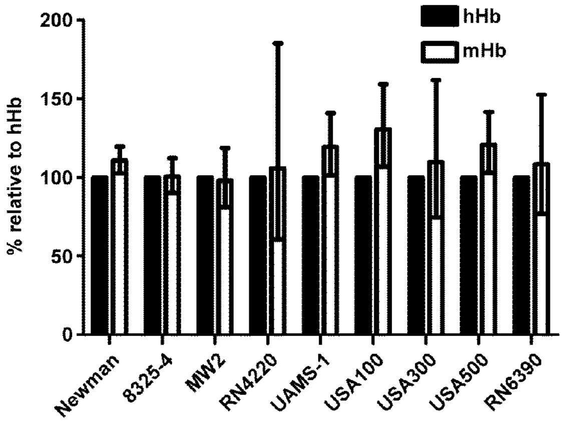
FIG. 8. Relative hHb and mHb binding by *S. aureus* strains grown in iron-replete conditions. Indicated strains of *S. aureus* were grown in iron-replete conditions, incubated with hemoglobin at indicated concentrations and washed. Captured hemoglobin was eluted, subjected to SDS-PAGE, and silver stained. Bound hemoglobin was quantified based on the relative intensity of Hb bands. Relative quantities of cell-wall bound hemoglobin are expressed as percent of bound hHb. Means and statistical significance were calculated based on logarithmically transformed fractions. Error bars represent confidence intervals ($\alpha=0.05$). Quantities of bound mHb were not statistically different from hHb supplemented at the same conditions (Student's two-tailed t-test, $P<0.05$). Each graph is the result of three independent experiments.
Figure 9:
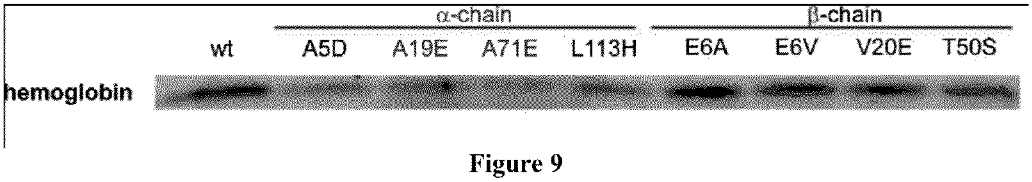
FIG. 9. Recombinant human hemoglobin variants were expressed and purified from BL21 (DE3) strain of *E. coli*. Iron-starved *S. aureus* strain Newman were incubated with hemoglobin and washed. Captured hemoglobin was eluted, subjected to SDS-PAGE, transferred and immunoblotted with anti-Hb antibody.

The experiments described above were performed using *S. aureus* Newman, a commonly studied laboratory strain. To assess the ability of other laboratory and clinically relevant *S. aureus* isolates to acquire iron from mHb and hHb the present inventors tested the Hb preference of a panel of staphylococcal strains. As demonstrated in FIG. 4A, all tested *S. aureus* isolates display increased binding of hHb as compared to mHb. Isogenic ΔisdB mutants of clinically relevant USA300 and the common laboratory strains RN4220 and RN6390 lost the ability to bind increased quantities of hHb as observed with strain Newman (FIGS. 4B and 1A). In support of the role of IsdB in increased hHb binding, *S. aureus* do not differentiate between hHb and mHb when grown under iron-replete conditions that prohibit isdB expression (FIG. 8). Further, disk diffusion assays demonstrated increased proliferation using hHb as a sole iron source as compared to mHb for all tested *S. aureus* strains (FIG. 4C). These results demonstrate that the preferential utilization of hHb as an iron source by IsdB is conserved among tested *S. aureus* isolates.

Numerous bacterial pathogens express hemoglobin receptors and utilize hemoglobin as an iron source during infection (Crosa et al., 2004). In keeping with this, the present inventors evaluated the ability of a number of bacterial species to grow in the presence of hHb and mHb. Many organisms that do not express hemoglobin receptors were unable to proliferate in the presence of either hHb or mHb, including *Escherichia coli* DH5α *Staphylococcus haemolyticus, Staphylococcus epidermidis* and *Shigella flexneri* (data not shown). In contrast, *Staphylococcus lugdunensis, Staphylococcus simulans* and *Corynebacterium diphtheriae* displayed a preference for hHb similar to *S. aureus* (FIG. 4D). Finally, *Acinetobacter baumannii, Pseudomonas aeruginosa, Bacillus anthracis* and *Bacillus cereus* utilized mHb and hHb with equal efficiency. These results demonstrate that the preferential utilization of hHb as an iron source is conserved across some bacterial pathogens while others do not discriminate between hHb and mHb.

DISCUSSION

*S. aureus* is a commensal organism that colonizes the anterior nares of approximately 30% of the human population (Weems, 2001). *S. aureus* is also capable of breaching these sites of initial colonization leading to significant morbidity and mortality (Klevens et al., 2007; Kuehnert et al., 2005). The host and bacterial factors that mediate this switch from commensal colonization to invasive disease are not understood. Herein, the present inventors demonstrate that human hemoglobin is a factor that impacts the host susceptibility to *S. aureus* through its interaction with the hemoglobin receptor IsdB. The significant affinity of IsdB for human hemoglobin permits the efficient utilization of hHb as an iron source leading to increased colonization and disease. Importantly, all tested clinically relevant strains displayed increased iron acquisition from hHb. By exploiting these observations, the present inventors have established $\alpha^{H}\beta^{A}$ mice as an improved murine model for studies into the pathogenesis of staphylococcal infections. These findings raise the exciting possibility that human hemoglobin polymorphisms may have implications regarding individual susceptibility to bacterial infections (Hardison et al., 2002).

These results revealed that a variety of distinct pathogens display an enhanced ability to utilize hHb as an iron source, while others do not exhibit hemoglobin preference (FIG. 4D). Notably, bacteria that primarily associate with humans (*S. aureus, S. lugdunensis, S. simulans, C. diphtheria*) display preference for hHb over mHb, whereas environmental bacteria that infect numerous hosts (*A. baumannii, P. aeruginosa, B. anthracis* and *B. cereus*) grow at comparable levels on hHb and mHb. In this regard, *S. aureus* IsdB binds hHb with a much stronger $K_D$ value ($5.5\times10^{-8}$ M) than the *B. anthracis* hemoglobin binding protein IsdX1 ($7.3\times10^{-6}$ M) (Maresso et al., 2008). This supports the hypothesis that *S. aureus* IsdB is optimized to bind hHb in order to acquire iron and colonize humans.

Much of what has been learned regarding the pathogenesis of *S. aureus* infection has been obtained from murine models of infection. However, due to inherent differences between mice and humans, murine infection models do not perfectly recapitulate human disease. To improve on this shortcoming, significant effort has been devoted to the development of humanized mouse models that more accurately reflect human disease (Legrand et al., 2009; Shultz et al., 2007). To date, few humanized mouse models have been established that exploit non-immune host factors (Johansson et al., 2003; Lecuit et al., 2001; Sun et al., 2004). The findings add the human hemoglobin expressing mouse to the list of humanized animals that are valuable tools for modeling infection. Moreover, these findings demonstrate that humanized mouse models can be created that exploit the nutrient requirements of bacterial pathogens. Importantly, many bacterial pathogens utilize hemoglobin as an iron source; therefore human hemoglobin expressing mice may be valuable for studies into a variety of infectious diseases (Crosa et al., 2004).

Experimental Procedures

Bacterial strains and growth conditions All experiments were carried out with *S. aureus* strain Newman (Duthie and Lorenz, 1952), or with mutants generated in its background, unless indicated otherwise. The following strains of other bacteria were used for growth assays: *Acenitobacter baumannii* 17978, *Psuedomonas aeruginosa* PAO1, *E. coli* DH5a, *Staphylococcus lugdunensis* HKU09-01, *Staphylococcus simulans* TNK3, *Staphylococcus epidermidis* NRS6, *Bacillus cereus* 569, *Bacillus anthracis* Sterne, *Staphylococcus haemolyticus* NRS9, *Corynebacterium diphtheriae* C7(−) and *Shigella flexneri* SC560 (an M90T derivative with a ΔicsA::ΩSp$^{r}$ mutation). All cultures were inoculated from a single colony and grown overnight (−20 hours) in 5 ml RPMI (Thermo) medium supplemented with 1% casamino acids (RPMI+CA) in 15 ml conical tubes at 37° C. with shaking at 180 rotations per minute (rpm) unless noted otherwise. The isogenic variant lacking isdB (ΔisdB) has been described previously (Mazmanian et al., 2003). A complementing plasmid containing isdB has also been previously described (Torres et al., 2006). Alanine substitution mutations within isdB at position Y165 were generated using Pfu mutagenesis and confirmed by sequencing. In order to maintain the plasmids, the complemented strains were grown in the presence of chloramphenicol (10 μg/ml). RN6390ΔisdB has been described previously (Taylor and Heinrichs, 2002). Strains inactivated for isdB in RN4220 and USA300 were generated by transducing the ΔisdB::ermC allele from Newman ΔisdB using bacteriophageϕ-85 (Mazmanian et al., 2003).

Purification of human and mouse hemoglobin Erythrocytes were sedimented by centrifugation (1,500×g, 20 minutes, 4° C.) from fresh human or mouse blood supplemented with anticoagulant. Erythrocytes were then washed 3 times with 3 volumes of ice cold saline (0.9% NaCl). Hemoglobin was released from erythrocytes by gently resuspending red blood cells in 1.5 volumes of 10 mM Tris-HCl (pH8.0) and 20% toluene (v/v) overnight on a rotisserie at 4° C. Hemolysate was separated from insoluble cellular debris (pellet) and membranes (toluene, upper layer) by a single centrifugation (20,000×g, 1 hour, 4)C.°. Hemolysate was then passed through a 0.4 μm filter. Hemoglobin was purified using an HPLC anion exchange column (Varian, PL-SAX 1000 Å 8 μm, 150 mm×4.6 mm). The mobile phase A was 10 mM Tris-HCl (pH 8.0) and mobile phase B was 10 mM Tris-HCl (pH 8.0)+0.5 M NaCl. A 0-100% gradient of solvent B was run over 2 minutes at 2.0 ml/min flow rate. The eluant was monitored based on absorption (λ: 410 nm and 280 nm). Purified hemoglobin was dialyzed twice at 4° C. against phosphate buffered saline (PBS). Final hemoglobin concentrations were measured by Drabkin's reagent (Sigma). Purified hemoglobin was stored in liquid nitrogen.

*S. aureus* hemoglobin binding assay Hemoglobin was either purified from blood (FIGS. 1 and 5B) or purchased (Sigma) (FIG. 5C). *S. aureus* was grown overnight in RPMI+CA supplemented with 0.5 mM of the iron chelator 2,2-dipyridyl (iron deplete) or 100 μM FeCl3 (iron replete). Bacterial numbers were normalized to an optical density at 600 nm (OD 600) of 2.0. One ml of each culture was sedimented by centrifugation (3,000×g, 10 minutes), resuspended in 1 ml of PBS containing the indicated concentrations of hemoglobin and incubated at 37° C. for 0.5 hour with shaking at 180 rpm. Upon completion of incubation, bacteria were washed 3 times with 1 ml of ice cold PBS, resuspended in 30 μl of 4% sodium dodecyl sulfate (SDS) 0.5M Tris-HCl (pH 8.0) and boiled for 5 minutes to release bound hemoglobin. *S. aureus* was then sedimented by centrifugation (16,000×g, 5 minutes) and the supernatant containing hemoglobin was collected. Solubilized hemoglobin was subjected to 15% SDS-PAGE electrophoresis. Gels were silver stained (GE Healthcare Kit) and the relative abundance of bound hemoglobin was estimated based on the density of hemoglobin bands quantified by the Odyssey infrared imaging system (LI-COR) at 800 nm.

Immunoblotting of cell wall IsdB Cell walls were solubilized by incubation of *S. aureus* in 20 μg/ml lysostaphin for 0.5 hour at 37 C.°. Cell wall proteins were separated by 12% SDS-PAGE and transferred onto nitrocellulose membranes. Membranes were blocked with 5% milk made in TBS with 0.1% TWEEN 20 (TBST) from 1 h to overnight. The membranes were then incubated in milk plus primary rabbit anti-IsdB (1:10,000), washed three times with TBST, incubated in milk plus 0.1% sodium dodecyl sulfate plus secondary ALEXA FLOUR 680 goat anti-rabbit IgG(H+ L) (1:25,000), and washed three times in TBST. Membranes were visualized using an Odyssey infrared imaging system (Li-Cor).

IsdB—hemoglobin affinity measurement Purification of recombinant IsdB has been previously described (Mazmanian et al., 2003). Hemoglobin was biotinylated using EZ-Link NHS-LC-LC-Biotin (Pierce) at 1:2 protein:biotin ratio according to manufacturer's recommendations. Unbound biotin was removed with Zeba™ Desalt Spin Columns (Pierce 89889). Binding kinetics were measured with an Octet QK (ForteBio, Inc., Menlo Park, Calif.) apparatus (FIG. 6). Briefly, streptavidin high binding capacity FA biosensors (ForteBio 18-5019) were loaded with biotinylated hemoglobin at 25 μg/ml. Upon washing in PBS the sensors were transferred to rIsdB solution (5-10,000 nM) to allow association between rIsdB and hemoglobin. The sensors were then transferred to PBS to measure dissociation. Dissociation constants were calculated using Origin 7.5 SR6 software (OriginLab Corp., Northampton, Mass.) based on data acquired from three experiments using an automated curve fitting prompted by the Octet 4 software (ForteBio).

Growth in liquid medium Single colonies of *S. aureus* were inoculated into RPMI+CA supplemented with 0.5 mM of the iron chelator ethylenediamine-di(o-hydroxyphenylacetic acid) (EDDHA, LGC Standards GmbH) and grown overnight. EDDHA was used in place of 2,2-dipyridyl due to the fact that EDDHA is less toxic to *S. aureus* in growth assays. One ml of overnight cultures was normalized to OD600 of 3.0, bacteria were sedimented (3,000×g, 10 minutes), and resuspended in 1 ml NRPMI+0.5 mM EDDHA. NRPMI was prepared in advance by treating RPMI+CA with Chelex 100 (Sigma) according to the manufacturer's recommendations and supplementing the resulting ion-deficient medium with 25 μM ZnCl2, 25 μM MnCl2, 100 μM CaCl2 and 1 mM MgCl2. The resulting suspension of *S. aureus* was subcultured (1:100) into 1 ml of NRPMI+0.5 mM EDDHA+hemoglobin at indicated concentrations. One ml cultures were incubated at 37° C. in 15 ml conical tubes on a rotating wheel. OD600 measurements were taken at indicated time-points by mixing 10 μl aliquots of the culture with 90 μl PBS in 96 well plates. The number of colony forming units per milliliter of culture were quantified by serial dilution and plating on tryptic soy agar.

Growth on solid medium Single colonies of bacteria were inoculated into RPMI+CA+EDDHA (500 μM for *S. aureus* strains and *P. aeruginosa,* 250 μM for *B. anthracis*, and *S. lugdunensis,* 100 μM for *A. baumannii, S. haemolyticus, S. simulans, E. coli*, and *S. flexneri,* 25 μM for *S. epidermidis,* 10 μM for *B. cereus* and none for *C. diphtheriae*) and grown overnight. Overnight cultures were spread with cotton swabs on NRPMI agar (NRPMI+1.2% Bacto Agar) supplemented with EDDHA (500 μM for *S. aureus strains, P. aeruginosa, B. anthracis, S. lugdunensis*, and *B. cereus,* 100 μM for *A. baumannii, S. haemolyticus, S. simulans, E. coli, S. flexneri*, and *S. epidermidis*). *C. diphtheriae* were grown on RPMI+CA agar supplemented with 1 μM EDDHA. Sterile Whatman (d=7 mm) disks were impregnated with 10 μl PBS-hemoglobin (1 mg/ml), placed onto agar and incubated at 37° C. Pictures were taken at a 72 hour time point except: USA500 at 96 hours, *B. cereus* at 14 hours, *B. anthracis* at 20 hours. Growth was measured by quantifying the distance between the edge of the disk and the edge of the zone of growth.

Systemic mouse infections Seven week old C57BL/6J or human hemoglobin transgenic $\alpha^H\beta^A$ mice that were hemizygous for the transgene (Romero et al., 2004), but had no knock-outs or deletions, were infected retroorbitaly with ~107 CFU grown to mid-log phase in tryptic soy broth and resuspended in sterile PBS. Ninety-six hours post infection the mice were euthanized with forced inhalation of $CO_2$. The hearts and livers were removed post mortem and homogenized in 1 ml sterile PBS. Organ suspensions were serially diluted, plated on tryptic soy agar and incubated overnight at 37° C. The following morning the numbers of CFU/organ were quantified. Animal experiments were approved by the institutional animal care and use committee of Vanderbilt University.

INCORPORATION BY REFERENCE

All publications, patents, and patent applications mentioned in this specification are herein incorporated by reference to the same extent as if each individual publication, patent, or patent application was specifically and individually indicated to be incorporated by reference, including the references set fort in the following list.

REFERENCES

1. Bullen, J. J. (1981). The significance of iron in infection. Rev. Infect. Dis. 3, 1127-1138.
2. Cheng, A. G., Kim, H. K., Burts, M. L., Krausz, T., Schneewind, O., and Missiakas, D. M. (2009). Genetic requirements for *Staphylococcus aureus* abscess formation and persistence in host tissues. Faseb J. 23, 3393-3404.
3. Crosa J. H., Mey A. R., and Payne S. M. (2004). Iron Transport in Bacteria (Washington, D.C.: A.S.M. Press).
4. Drabkin, D. (1951). Metabolism of the Hemin Chromoproteins. Physiological Reviews 31, 345-431.
5. Dryla, A., Hoffmann, B., Gelbmann, D., Giefing, C., Hanner, M., Meinke, A., Anderson, A. S., Koppensteiner, W., Konrat, R., von Gabain, A., and Nagy, E. (2007). High-affinity binding of the staphylococcal HarA protein to haptoglobin and hemoglobin involves a domain with an antiparallel eight-stranded beta-barrel fold. J. Bacteriol. 189, 254-264.
6. Duthie, E. S., and Lorenz, L. L. (1952). Staphylococcal coagulase; mode of action and antigenicity. J. Gen. Microbiol. 6, 95-107.
7. Hardison, R. C., Chui, D. H., Giardine, B., Riemer, C., Patrinos, G. P., Anagnou, N., Miller, W., and Wajcman, H. (2002). HbVar: A relational database of human hemoglobin variants and thalassemia mutations at the globin gene server. Hum. Mutat. 19, 225-233.
8. Johansson, L., Rytkonen, A., Bergman, P., Albiger, B., Kallstrom, H., Hokfelt, T., Agerberth, B., Cattaneo, R., and Jonsson, A. B. (2003). CD46 in meningococcal disease. Science 301, 373-375.
9. Klevens, R. M., Morrison, M. A., Nadle, J., Petit, S., Gershman, K., Ray, S., Harrison, L. H., Lynfield, R., Dumyati, G., Townes, J. M., et al. (2007). Invasive methicillin-resistant *Staphylococcus aureus* infections in the United States. Jama 298, 1763-1771.
10. Kuehnert, M. J., Hill, H. A., Kupronis, B. A., Tokars, J. I., Solomon, S. L., and Jernigan, D. B. (2005). Methicillin-resistant-*Staphylococcus aureus* hospitalizations, United States. Emerg. Infect. Dis. 11, 868-872.
11. Lecuit, M., Vandormael-Pournin, S., Lefort, J., Huerre, M., Gounon, P., Dupuy, C., Babinet, C., and Cossart, P. (2001). A transgenic model for listeriosis: role of internalin in crossing the intestinal barrier. Science 292, 1722-1725.
12. Legrand, N., Ploss, A., Balling, R., Becker, P. D., Borsotti, C., Brezillon, N., Debarry, J., de Jong, Y., Deng, H., Di Santo, J. P., et al. (2009). Humanized mice for modeling human infectious disease: challenges, progress, and outlook. Cell Host Microbe 6, 5-9.
13. Maresso A. W., Garufi G., and Schneewind O. (2008). *Bacillus anthracis* secretes proteins that mediate heme acquisition from hemoglobin. PLoS Pathog. 4, e1000132Mazmanian, S. K., Liu, G., Jensen, E. R., Lenoy, E., and Schneewind, O. (2000). *Staphylococcus aureus* sortase mutants defective in the display of surface proteins and in the pathogenesis of animal infections. Proc. Natl. Acad. Sci. USA 97, 5510-5515.

14. Mazmanian, S. K., Skaar, E. P., Gaspar, A. H., Humayun, M., Gornicki, P., Jelenska, J., Joachmiak, A., Missiakas, D. M., and Schneewind, O. (2003). Passage of heme-iron across the envelope of *Staphylococcus aureus*. Science 299, 906-909.

15. Muryoi, N., Tiedemann, M. T., Pluym, M., Cheung, J., Heinrichs, D. E., and Stillman, M. J. (2008). Demonstration of the iron-regulated surface determinant (Isd) heme transfer pathway in *Staphylococcus aureus*. J. Biol. Chem. 283, 28125-28136.

16. Pishchany, G., Dickey, S. E., and Skaar, E. P. (2009). Subcellular localization of the *Staphylococcus aureus* heme iron transport components IsdA and IsdB. Infect. Immun. 77, 2624-2634.

17. Reniere, M. L., and Skaar, E. P. (2008). *Staphylococcus aureus* haem oxygenases are differentially regulated by iron and haem. Mol. Microbiol. 69, 1304-1315.

18. Reniere, M. L., Torres, V. J., and Skaar, E. P. (2007). Intracellular metalloporphyrin metabolism in *Staphylococcus aureus*. Biometals 20, 333-345.

19. Reniere, M. L., Ukpabi, G. N., Harry, S. R., Stec, D. F., Krull, R., Wright, D. W., Bachmann, B. O., Murphy, M. E., and Skaar, E. P. (2010). The IsdG-family of haem oxygenases degrades haem to a novel chromophore. Mol. Microbiol. 75, 1529-1538.

20. Romero, J. R., Suzuka, S. M., Nagel, R. L., and Fabry, M. E. (2004). Expression of HbC and HbS, but not HbA, results in activation of K-Cl cotransport activity in transgenic mouse red cells. Blood 103, 2384-2390.

21. Shultz, L. D., Ishikawa, F., and Greiner, D. L. (2007). Humanized mice in translational biomedical research. Nat. Rev. Immunol. 7, 118-130.

22. Skaar, E. P., Humayun, M., Bae, T., DeBord, K. L., and Schneewind, O. (2004). Iron-source preference of *Staphylococcus aureus* infections. Science 305, 1626-1628.

23. Sun, H., Ringdahl, U., Homeister, J. W., Fay, W. P., Engleberg, N.C., Yang, A. Y., Rozek, L. S., Wang, X., Sjobring, U., and Ginsburg, D. (2004). Plasminogen is a critical host pathogenicity factor for group A streptococcal infection. Science 305, 1283-1286.

24. Taylor J. M., and Heinrichs D. E. (2002). Transferrin binding in *Staphylococcus aureus*: involvement of a cell wall-anchored protein. Mol. Microbiol. 43, 1603-1614.

25. Torres, V. J., Attia, A. S., Mason, W. J., Hood, M. I., Corbin, B. D., Beasley, F. C., Anderson, K. L., Stauff, D. L., McDonald, W. H., Zimmerman, L. J., et al. (2010). *Staphylococcus aureus* Fur regulates the expression of virulence factors that contribute to the pathogenesis of pneumonia. Infect. Immun. 78, 1618-1628.

26. Torres, V. J., Pishchany, G., Humayun, M., Schneewind, 0., and Skaar, E. P. (2006). *Staphylococcus aureus* IsdB is a hemoglobin receptor required for heme iron utilization. J. Bacteriol. 188, 8421-8429.

27. Weems, J. J., Jr. (2001). The many faces of *Staphylococcus aureus* infection. Recognizing and managing its life-threatening manifestations. Postgrad. Med. 110, 24-26, 29-31, 35-26.

28. Ye L., Chang J. C., Lu R., and Kan Y. W. (2008). High oxygen environment during pregnancy rescues sickle cell anemia mice from prenatal death. Blood Cells Mol. Dis. 41, 67-72.

29. Zhu, H., Xie, G., Liu, M., Olson, J. S., Fabian, M., Dooley, D. M., and Lei, B. (2008). Pathway for heme uptake from human methemoglobin by the iron-regulated surface determinants system of *Staphylococcus aureus*. J. Biol. Chem. 283, 18450-18460.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of screening a mammalian subject for susceptibility to systemic infection by *Staphylococcus aureus* comprising:

(a) providing purified hemoglobin from the subject;

(b) contacting the hemoglobin with the *Staphylococcus aureus* and (c) measuring the binding affinity between the hemoglobin and the *Staphylococcus aureus*, wherein an increased binding affinity between the hemoglobin and the *Staphylococcus aureus* compared to the binding affinity between the hemoglobin and a control is indicative of the enhanced susceptibility of the subject to the *Staphylococcus aureus*, wherein the control is an average of binding affinities between the *Staphylococcus aureus* and purified hemoglobin from a predetermined population of the mammalian subject.

2. The method of claim 1, wherein the subject is human.

3. The method of claim 1, wherein the increased binding affinity is indicative of iron acquisition by the *Staphylococcus aureus*.

4. The method of claim 1, wherein the increased binding affinity is indicative of risk of developing the infection by the subject.

5. The method of claim 1, wherein the increased binding affinity is indicative of risk of developing the exacerbated infection by the subject.

* * * * *